United States Patent
Revellat et al.

(10) Patent No.: US 12,168,115 B2
(45) Date of Patent: Dec. 17, 2024

(54) LIQUID MEDICAMENT ADMINISTRATION DEVICE

(71) Applicant: Sanofi-Aventis Deutschland GmbH, Frankfurt am Main (DE)

(72) Inventors: Hugo Revellat, Hertfordshire (GB); Thomas Mark Kemp, Hertfordshire (GB); Robbie Wilson, Hertfordshire (GB); Paul Edward Jansen, Boston, MA (US); Marc Schader, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 616 days.

(21) Appl. No.: 16/343,504

(22) PCT Filed: Oct. 20, 2017

(86) PCT No.: PCT/EP2017/076875
§ 371 (c)(1),
(2) Date: Apr. 19, 2019

(87) PCT Pub. No.: WO2018/073424
PCT Pub. Date: Apr. 26, 2018

(65) Prior Publication Data
US 2019/0262540 A1    Aug. 29, 2019

(30) Foreign Application Priority Data
Oct. 21, 2016    (EP) .................................... 16194956

(51) Int. Cl.
*A61M 5/31*    (2006.01)
*A61M 5/20*    (2006.01)
(Continued)

(52) U.S. Cl.
CPC ................ *A61M 5/31* (2013.01); *A61M 5/20* (2013.01); *A61M 5/24* (2013.01); *A61M 5/3129* (2013.01);
(Continued)

(58) Field of Classification Search
CPC ........ A61M 5/31; A61M 5/24; A61M 5/3129; A61M 2005/3125; A61M 2205/583;
(Continued)

(56) References Cited

U.S. PATENT DOCUMENTS

| 4,884,120 A | 11/1989 | Mochizuki et al. |
| 6,241,709 B1 | 6/2001 | Bechtold et al. |

(Continued)

FOREIGN PATENT DOCUMENTS

| CN | 102056639 | 5/2011 |
| CN | 102089024 | 6/2011 |

(Continued)

OTHER PUBLICATIONS

PCT International Preliminary Report on Patentability in International Appln. No. PCT/EP2017/076875, dated Apr. 23, 2019, 6 pages.

(Continued)

*Primary Examiner* — Lauren P Farrar
(74) *Attorney, Agent, or Firm* — Fish & Richardson P.C.

(57) ABSTRACT

A liquid medicament administration device includes a body configured to contain and support a medicament container. The body includes an aperture. The aperture includes a viewing window that is coincident with the medicament container when the medicament container is present. The device is configured such that the viewing window is size-adjustable. Also disclosed are associated methods of manufacture.

26 Claims, 7 Drawing Sheets

(51) Int. Cl.
*A61M 5/24* (2006.01)
*A61M 5/315* (2006.01)

(52) U.S. Cl.
CPC . *A61M 5/31545* (2013.01); *A61M 2005/2403* (2013.01); *A61M 2005/2477* (2013.01); *A61M 2005/3125* (2013.01); *A61M 2005/3142* (2013.01); *A61M 2205/583* (2013.01); *A61M 2207/00* (2013.01)

(58) Field of Classification Search
CPC .............. A61M 2207/00; A61M 5/20; A61M 2005/2403; A61M 2005/2477; A61M 2005/3142
See application file for complete search history.

(56) References Cited

U.S. PATENT DOCUMENTS

| | | | |
|---|---|---|---|
| 2006/0184117 | A1 | 8/2006 | Knight et al. |
| 2007/0244444 | A1 | 10/2007 | Guelker et al. |
| 2008/0051729 | A1 | 2/2008 | Cheng |
| 2008/0269688 | A1* | 10/2008 | Colucci ............. A61M 5/31551 604/189 |
| 2009/0182284 | A1 | 7/2009 | Morgan |
| 2010/0274198 | A1 | 10/2010 | Bechtold |
| 2011/0313364 | A1* | 12/2011 | Rolfe ................. A61M 5/2033 604/198 |
| 2013/0012884 | A1* | 1/2013 | Pommerau ............. A61J 1/062 604/189 |
| 2013/0079718 | A1* | 3/2013 | Shang ..................... A61M 5/20 604/131 |
| 2013/0090605 | A1 | 4/2013 | O'Connor et al. |
| 2013/0204229 | A1* | 8/2013 | Olson ................. A61M 5/3243 604/218 |
| 2015/0065960 | A1* | 3/2015 | Osman .................... A61M 5/24 604/189 |
| 2016/0068326 | A1 | 3/2016 | Le Maner et al. |
| 2016/0193428 | A1* | 7/2016 | Perthu ................. A61M 5/3204 604/506 |
| 2017/0266384 | A1* | 9/2017 | Veasey .................... A61M 5/20 |
| 2017/0326303 | A1* | 11/2017 | Eardley ............. A61M 5/31543 |

FOREIGN PATENT DOCUMENTS

| | | |
|---|---|---|
| CN | 102284106 | 12/2011 |
| CN | 102448520 | 5/2012 |
| CN | 103533975 | 1/2014 |
| CN | 203379434 | 1/2014 |
| CN | 104138627 | 11/2014 |
| CN | 104203313 | 12/2014 |
| CN | 104984438 | 10/2015 |
| CN | 105050644 | 11/2015 |
| CN | 105473173 | 4/2016 |
| CN | 105492049 | 4/2016 |
| CN | 105530970 | 4/2016 |
| CN | 105705185 | 6/2016 |
| CN | 105939746 | 9/2016 |
| CN | 105705187 | 6/2022 |
| EP | 2957307 | 12/2015 |
| JP | S62-194644 | 8/1987 |
| JP | H01-98608 | 6/1989 |
| JP | H03-2259 Y2 | 1/1991 |
| JP | 2011-528247 | 11/2011 |
| JP | 2012-513271 | 6/2012 |
| JP | 2014-506493 | 3/2014 |
| KR | 2015-515318 | 5/2015 |
| WO | WO 2007/129106 | 11/2007 |
| WO | WO 2009/126435 | 10/2009 |
| WO | WO 2010/003569 | 1/2010 |
| WO | WO 2010/007395 | 1/2010 |
| WO | WO 2010/072700 | 7/2010 |
| WO | WO 2010/076569 | 7/2010 |
| WO | WO 2010/110712 | 9/2010 |
| WO | WO 2011/146166 | 11/2011 |
| WO | WO 2012/065965 | 5/2012 |
| WO | WO 2012/103141 | 8/2012 |
| WO | WO 2013/149980 | 10/2013 |
| WO | WO 2014/122782 | 8/2014 |
| WO | WO 2015/007809 | 1/2015 |
| WO | WO 2015/014363 | 2/2015 |
| WO | WO 2015/028440 | 3/2015 |
| WO | WO 2015/113969 | 8/2015 |
| WO | WO 2016/083347 | 6/2016 |
| WO | WO 2016/091978 A1 | 6/2016 |
| WO | WO 2016/150898 | 9/2016 |

OTHER PUBLICATIONS

PCT International Search Report and Written Opinion in International Appln. No. PCT/EP2017/076875, mailed May 4, 2018, 8 pages.

* cited by examiner

LIQUID MEDICAMENT ADMINISTRATION DEVICE

CROSS REFERENCE TO RELATED APPLICATIONS

The present application is the national stage entry of International Patent Application No. PCT/EP2017/076875, filed on Oct. 20, 2017, and claims priority to Application No. EP 16194956.5, filed on Oct. 21, 2016, the disclosures of which are incorporated herein by reference.

TECHNICAL FIELD

The present disclosure relates to a liquid medicament administration device.

BACKGROUND

Liquid medicament administration devices, such as auto-injector devices, can take various forms. Typically, they include one or more windows to enable the quantity of medicament in the device to be viewed as the medicament is administered. For example, a piston in a syringe may be viewed as a piston rod is depressed.

SUMMARY

In a first aspect, a liquid medicament administration device is provided, comprising a body configured to contain and support a medicament container; wherein the body comprises an aperture; wherein the aperture comprises a viewing window that is coincident with the medicament container when the medicament container is present; and wherein the device is configured such that the viewing window is size-adjustable.

A machine or an assembly worker is therefore able to adjust the size of the viewing window in relation to the initial quantity of medicament in the medicament container, for example to obscure empty portions of the medicament container. A single device is therefore provided which may be configured to accommodate a range of medicament volumes. The body may be manufactured as a single piece, e.g. as a moulding. A single manufactured component can therefore be adapted to accommodate medicament containers of the same size but having a variety of initial medicament volumes. This allows both the device and the medicament container to be standardised such that the same device and medicament container type can be used irrespective of the medicament volume to be administered. Accordingly no redesign or retooling is required for different applications. Typically the device is configured such that the viewing window is size-adjustable during the assembly of the device, but not size-adjustable by the end-user. Undesirable alteration of the viewing window by the end user or third parties is thereby prevented.

The body may be configured to directly contain and support the medicament container. Alternatively the body may be configured to indirectly contain and support the medicament container. For example, the body may be configured to contain and support an inner carrier which in turn is configured to contain and support the medicament container.

The medicament container may be a syringe or a cartridge, such as a sealed vial or a flexible cartridge. Typically the medicament container is a syringe, such as a syringe comprising a hollow cylinder for storing the medicament, a piston moveable within the cylinder, a piston rod connected to the piston for operating the piston, and an exit port in fluid communication with the inside of the cylinder, wherein the exit port is located distal to the piston.

Optionally, the medicament container may be configured such that the interior of the medicament container is visible via the viewing window when the medicament container is present in the device. For instance, one or more walls defining the medicament container may be transparent, wherein at least one transparent wall is coincident with the viewing window when the medicament container is present in the device. Where the medicament container is a syringe as described above, typically the hollow cylinder is transparent.

In one embodiment, the viewing window is configured to enable the quantity of medicament in the medicament container, when present, to be viewed. The medicament per se may be viewed and/or an indicator specifying the medicament quantity may be viewed. By enabling the medicament per se to be viewed the end user is able to check for contamination or degradation of the medicament, and/or check for unwanted air bubbles in the medicament. Delivery of a sub-optimal medicament is thereby prevented. In other embodiments however an indicator specifying the medicament quantity may be viewed but the medicament per se may not be visible. For example, where the medicament container is a syringe an indicator attached to the piston rod may be viewed. Such an embodiment may be used for medicaments where the speed of delivery is essential, to avoid undue delay in administration caused by the end user checking the medicament.

The body of the device may comprise two or more apertures each comprising a separate viewing window that is coincident with the medicament container when the medicament container is present. Typically, the device comprises two such apertures located on opposing faces of the device. This enables the end user to view the medicament and/or the quantity of medicament in the container without having to align the device in a particular direction.

Typically, the device is configured such that the size of the viewing window may be adjusted in relation to the quantity of medicament in the container. Optionally the size of the viewing window may be adjustable by one or more preformed elements. For example, the device may comprise an insertable or removable element configured to obscure an empty portion of the medicament container.

Where the medicament container is a syringe, the device may be configured such that the size of the viewing window may be adjusted to obscure the piston rod when the syringe contains the desired liquid medicament volume to be administered. Optionally, the viewing window may be adjusted to obscure the piston and the piston rod when the syringe contains the desired liquid medicament volume to be administered. Such configurations avoid unintentional confusion, concern or irritation to the end users of the device, who may mistakenly believe that an inadequate dosage is supplied if the piston rod and/or piston is visible in the viewing window pre-administration. The device may also be configured such that the size of the viewing window may be adjusted to enable the piston to be viewed as the piston rod is depressed during the administration of the medicament. In one embodiment, the device may be configured such that the size of the viewing window may be adjusted to enable the piston to be viewed when the piston rod is fully depressed. Alternatively, the device may be configured such that the size of the viewing window may be adjusted to obscure the piston when the piston rod is fully depressed. Thus, an embodiment may be provided wherein the device is configured such that the size of the viewing window may be adjusted to obscure the piston when the syringe contains the desired liquid medicament volume to be administered and when the piston rod is fully depressed, but to enable the piston to be viewed at all intermediate positions, i.e. as the piston rod is depressed. This embodiment allows facile verification by the end user of the extent of administration and further avoids unintentional confusion, concern or irritation pre-administration as discussed above.

Typically, the device is configured such that the size-adjustment is single-use, i.e. the size of the viewing window is irreversibly adjusted. This prevents interference with the viewing window after the assembly process.

The device may comprise a proximal end and a distal end, with a longitudinal axis extending from the proximal end to the distal end, optionally wherein the aperture is elongate and positioned parallel to the longitudinal axis of the device. Typically, the elongate aperture is positioned between the proximal end of the device and the midway point between the proximal and distal ends of the device.

In one embodiment, the aperture is configured to receive one or more inserts, wherein said one or more inserts when present partially obscure the aperture so as to reduce the size of the viewing window.

The aperture may be configured to receive a plurality of inserts. Alternatively, the aperture may be configured to receive a single insert, optionally wherein single inserts of varying sizes may be received. Typically, the one or more inserts obscure the distal end of the aperture.

While it is envisaged that in most embodiments said one or more inserts are opaque, in some embodiments at least one insert may be partially opaque and partially transparent, or the device may be configured to receive a plurality of inserts wherein at least one of the inserts is opaque and at least one of the inserts is transparent. In such embodiments, the viewing window may be coincident with the transparent inserts or the transparent portions of the inserts. Optionally, the medicament and/or the quantity of medicament in the container may be viewed through a transparent insert or a transparent portion of an insert. For example, the aperture may be configured to receive a single insert comprising a transparent portion and an opaque portion, wherein the insert traverses the entire aperture.

The one or more inserts and the body may comprise cooperating features to enable the inserts to be fixed within the aperture. Typically the cooperating features are not accessible from the exterior of the device after the inserts have been fixed within the aperture. Optionally the cooperating features enable a push-fit of the inserts in a direction approximately orthogonal to the surface of the body. The use of such cooperating features facilitates the rapid and facile fixture of the inserts by a machine or an assembly worker during the assembly of the device.

The one or more inserts may comprise one or more resilient tabs that engage in one or more corresponding recesses in one or more side walls defining the aperture. Typically, the resilient tabs are depressed as the one or more inserts enter the aperture, before the tabs expand into their corresponding recesses as a pre-set position is reached, thereby locking the one or more inserts into position.

Alternatively or in addition, the side walls of the aperture may comprise one or more resilient tabs that engage in one or more corresponding recesses in the inserts.

The aperture may be elongate and comprise a first side wall and a second side wall, wherein each of the first and second side walls extend in an approximately parallel direction relative to a longitudinal axis of the device, wherein the first side wall comprises a first recess for engaging a first resilient tab and the second side wall comprises a second recess for engaging a second resilient tab, and wherein a first insert comprises both the first and the second resilient tabs.

Optionally each of the first and second side walls has a surface that lies in a plane that extends in an approximately parallel and radial direction relative to the longitudinal axis of the device.

The longitudinal length of at least one recess in one side wall may substantially correspond to the length of the corresponding resilient tab that engages with the recess, such that the insert attached to the resilient tab is prevented from moving in a longitudinal direction. Thus, the number of cooperating features is minimised, reducing the complexity of the insert. Such an arrangement of the resilient tab and the recess may further predetermine the exact position of the insert within the aperture, simplifying the assembly process.

Alternatively, the first and the second recesses may together form a track extending in an approximately longitudinal direction relative to the longitudinal axis of the device, wherein the first and second resilient tabs of the first insert are able to engage with the track at any position along its length, and wherein the first insert further comprises a coupling element adapted to engage with a corresponding coupling element at a terminal end of the aperture, optionally via one or more intermediate inserts, so as to prevent movement of the first insert in a longitudinal direction. Such an arrangement allows the viewing window of a single body component to be adjusted to accommodate a variety of longitudinal dimensions using just two types of standardised insert. A modular system is thereby created. By using a single first insert a first longitudinal dimension may be obtained. By further including one or more standardised intermediate inserts, a plurality of longitudinal dimensions less than the first longitudinal dimension are obtainable, depending on the number of intermediate inserts used. The ability to obtain such variation with just two types of insert greatly reduces manufacturing costs when the manufacture of liquid medicament administration devices with different sizes of viewing window is desired.

Optionally, the coupling element and the corresponding coupling element are connectable by push-fitting the first insert in a direction approximately orthogonal to the surface of the body. For example the coupling element and the corresponding coupling element may comprise a male coupling and a corresponding female coupling, or vice-versa, such as hook and a corresponding hole for receiving the hook, or a T-piece and corresponding cut-out for receiving the T-piece. This enables the coupling elements and the resilient tabs/recesses to be engaged simultaneously in the same push-fit action, leading to efficiencies in assembly, especially machine assembly.

Typically the terminal end of the aperture comprising the corresponding coupling element is the distal end of the aperture.

The aperture may be further configured to receive one or more intermediate inserts, wherein each intermediate insert comprises a coupling element that is substantially identical to the coupling element of the first insert, and a corresponding coupling element that is substantially identical to the corresponding coupling element at the terminal end of the aperture. Optionally each intermediate insert further comprises a first resilient tab for engaging with the first recess and a second resilient tab for engaging with the second recess.

The dimensions of the size-adjusted viewing window may be defined partially by the edges of the aperture and partially by the edge of an insert.

Alternatively, one of the inserts may comprise an aperture which exclusively defines the dimensions of the size-adjusted viewing window.

Optionally, the body forms the outer case of the device.

The body may comprise one or more removable segments adjacent to the aperture, wherein the removable segments are configured to extend the aperture on removal so as to increase the size of the viewing window. A single-piece manufactured body, e.g. a moulding, may therefore be provided such that the removable inserts can be removed by a machine or an assembly worker to adjust the viewing window to the desired dimensions. Such a single manufactured component is therefore able to be adapted to accommodate medicament containers having a variety of initial medicament volumes.

Typically, the body comprises a plurality of removable segments. Typically, the removable segments are opaque.

Where the aperture is elongate and positioned parallel to the longitudinal axis of the device, the one or more removable segments may be located at the distal end of the aperture, such that on removal the aperture is extended in a distal direction.

The removable segments may be attached to the body via breakable elements. The use of breakable elements simplifies the assembly process, allowing the removable segments to be broken off or punched out by a machine or assembly worker. The use of breakable elements further allows the body and the removable segments to be manufactured as a single component, e.g. out of plastic in a single moulding.

Where the body comprises one or more removable segments, the body may form an inner carrier within an outer case, wherein the outer case comprises a second aperture, and wherein both the aperture of the body and the second aperture of the outer case comprise the viewing window.

In such a configuration, the dimensions of the size-adjusted viewing window may be defined entirely by the dimensions of the aperture of the inner carrier after the removal of the desired number of segments. Alternatively, the dimensions of the size-adjusted viewing window may be defined partially by the dimensions of the second aperture in the outer case and partially by the dimensions of the aperture of the inner carrier (body) after the removal of the desired number of segments.

The second aperture may be configured such that when the inner carrier is located within the outer case, the removal of any remaining removable segments from the inner carrier is prevented. For example, the tangential width of the removable segments may be greater than the tangential width of the second aperture. Alternatively bars may be provided at intervals extending tangentially across the second aperture. This prevents further removal of any remaining segments by the end user.

The device may comprise a medicament container containing a medicament. For example, the device may comprise a syringe containing a medicament.

The device may be an auto-injector device.

In a second aspect, a method of manufacturing a liquid medicament administration device comprises
 providing a liquid medicament administration device comprising a body configured to contain and support a medicament container, wherein the body comprises an aperture, wherein the aperture comprises a viewing window that is coincident with the medicament container when the medicament container is present; and
 adjusting the size of the viewing window.

The liquid medicament administration device and medicament container of the second aspect of the disclosure may be as described in relation to the first aspect of the disclosure.

BRIEF DESCRIPTION OF THE FIGURES

Exemplary embodiments are described with reference to the accompanying drawings, in which.

DETAILED DESCRIPTION

Exemplary embodiments of the current disclosure provide a liquid medicament administration device in which the size of a viewing window for viewing the quantity of medicament in the device may be adjusted during manufacture.

Such devices may be used to administer a wide range of liquid medicaments where the dosage of liquid medicament administered may vary considerably. For manufacturing purposes it is desirable to provide a device that is suitable for use with a wide variety of medicament types and dosage amounts. Thus, it is known to provide a large viewing window of a set size, which allows for large and small variations in the dosage amount to be viewed. However, where a small dosage amount is required this leads to the utilisation of only a small portion of the viewing window, with the remainder being superfluous to requirements. In the case of a syringe for example, where a small volume is used in a syringe of greater capacity, a remaining unused portion of the syringe will be visible via the viewing window. In particular, the piston and/or piston rod of the syringe may be visible through the viewing window prior to the administration of the medicament. This can cause concern by the end-user that the device is part-empty, i.e. that an insufficient dosage is being administered. At worst, this concern may lead to repeat attempts to administer the drug from numerous devices, resulting in an overdose of the administered drug.

To overcome the above difficulties, different designs of administration devices may be provided with viewing windows of different dimensions or with syringes of different diameter to accommodate varying quantities of medicament. However, such variation in design significantly increases manufacturing costs and complexity. The present disclosure overcomes at least these difficulties by providing a single device that can be rapidly configurable for a range of medicament volumes.

Figures 1A, 1B:
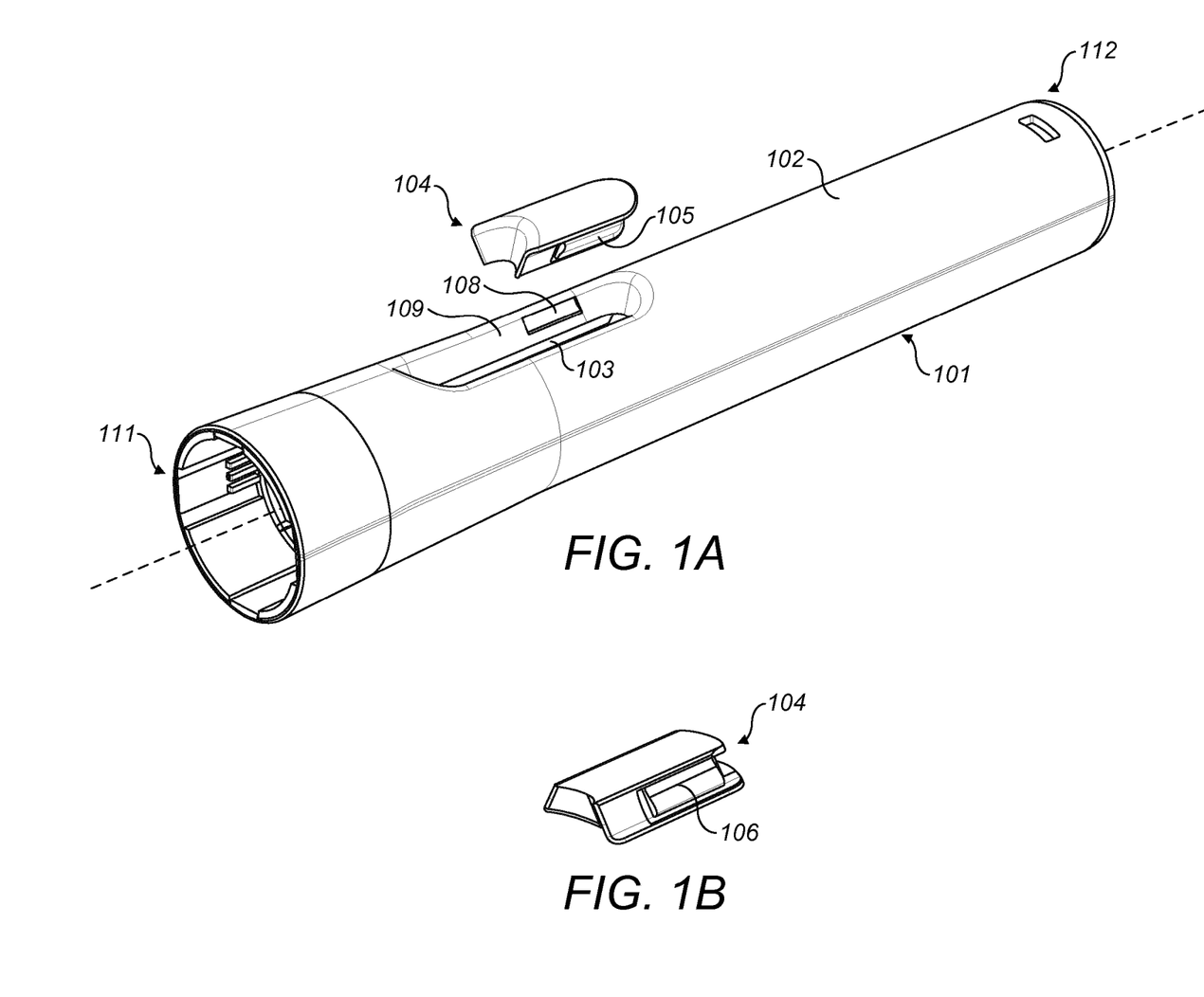
FIG. 1A is a perspective view of a first liquid medicament administration device and a corresponding insert.
FIG. 1B is a perspective view of the reverse side of the insert of FIG. 1A.
Figure 1C:
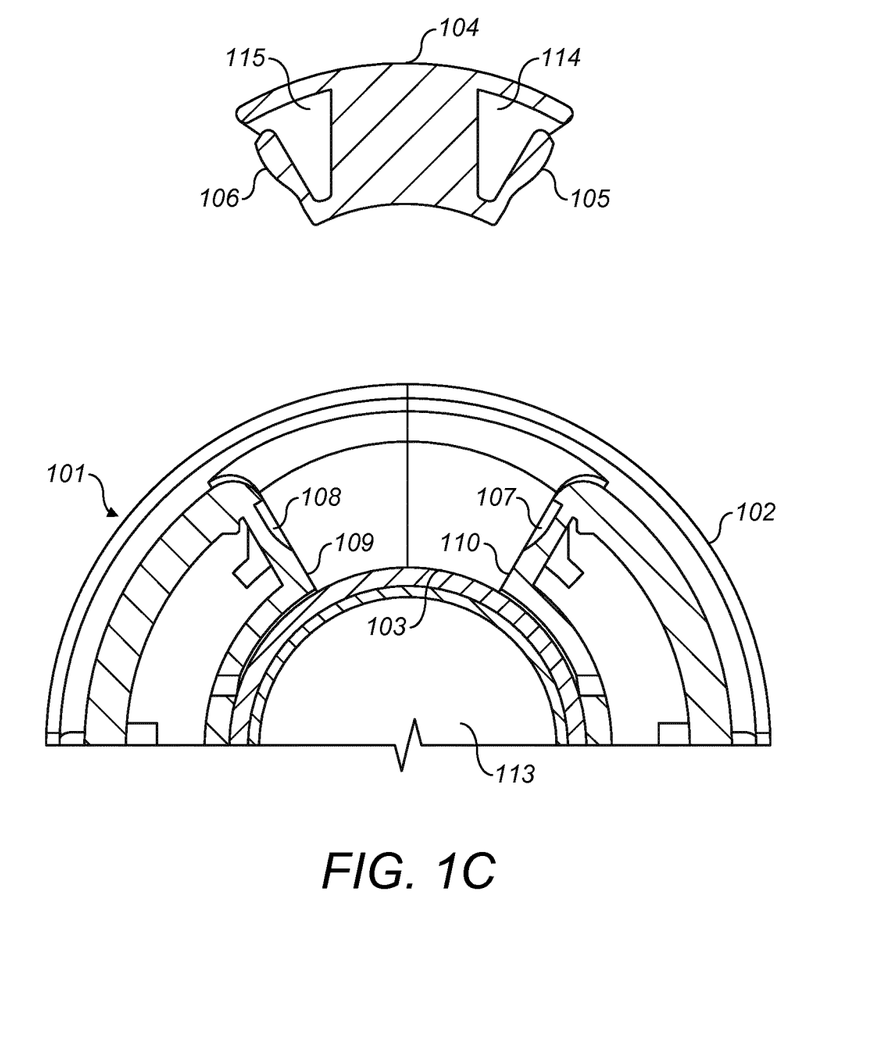
FIG. 1C is a partial cross-sectional view through the first device and insert at the point of attachment of the insert.

According to one aspect of the present disclosure a first exemplary liquid medicament administration device 101 is shown in FIGS. 1A, 1B and 1C. Device 101 as described above comprises a body 102 which also forms the outer case of the device and is configured to contain and support a medicament container such as a syringe (not shown). When in position the medicament container resides in the interior of the body in the cavity indicated by 113 in FIG. 1C. The body comprises an aperture 103 which defines a viewing window through which the medicament container may be viewed when present. The device further comprises an insert 104 which may be placed in the aperture 103 so as to reduce the size of the aperture and partially obscure the view of the medicament container. Thus, once in position, the insert 104 reduces the size of the viewing window.

Typically the insert 104 is placed in the aperture during the manufacture of the device so as to select an appropriate size viewing window in consideration of the amount of medicament in the medicament container. Empty portions of the medicament container may thereby be obscured to avoid confusion to the end user.

The medicament container is typically a syringe comprising a piston (also referred to as a plunger or a stopper). The piston may be observed via the viewing window. Typically the size of the viewing window is selected so as to essentially correspond to the longitudinal travel of the piston within the syringe upon administration. As will be appreciated, the greater the volume of medicament within a given syringe, the greater the longitudinal travel of the piston upon administration. Thus, a greater medicament volume will require a longer viewing window than a smaller medicament volume.

To hold the insert 104 in position, the insert 104 comprises resilient tabs 105 & 106, which engage in corresponding recesses 107 & 108 in the side walls 109 & 110 of the aperture 103. The resilient tabs are thin and rectangular in shape. Relative to the longitudinal axis of the device when the insert 104 is fixed in position, the resilient tabs 105 & 106 have a longitudinal dimension which is greater than their radial dimension which in turn is greater than their tangential dimension.

It will be noted that the side walls 109 & 110 are angled relative to each other, such that each opposing side wall extends in an approximately radial direction from the centre of the device. This facilitates the positioning of the inserts with ease on manufacture.

As illustrated in FIG. 1C the resilient tabs 105 & 106 are positioned on the tangential edges of the insert 104 and are attached to the reminder of the insert at a point proximal to the longitudinal axis of the device when inserted. The resilient tabs 105 & 106 are bulbous in cross-section, with their greatest tangential dimension occurring at a point distal to their point of attachment. The bulbous cross-sections correspond to concave cross-sections of the recesses 107 & 108. The resilient tabs are formed from a flexible and resilient material, e.g. plastic, that endows the tabs with their resilient nature.

The insert 104 further comprises cavities 114 & 115 located inboard of the resilient tabs 105 & 106, such that when the insert is pressed into position the resilient tabs may be temporarily deformed inwards into the cavities, before springing outwards into the corresponding recesses 107 & 108, thereby holding the insert in position.

The above-described arrangement of the resilient tabs 105 & 106 and the corresponding recesses 107 & 108 hinders removal of the insert 104 once attached to the body 102. Once in position, there is no access to the resilient tabs 105 & 106 and accordingly the resilient tabs cannot be depressed to facilitate removal. Thus, the insert 104 may only be removed by breakage of the insert 104 and/or the body 102. This discourages interference with the size of the viewing window by the end user or intermediaries.

As shown, the body or outer case 102 is substantially cylindrical and has a substantially constant diameter along the longitudinal axis X. That said, the three-dimensional configuration of the body or outer case is not critical and other typically elongate three-dimensional structures may be envisaged, such as those having a substantially square or hexagonal cross-section, and/or those which differ in their diameter and/or cross-sectional shape along their longitudinal axis.

FIG. 1B shows an insert 104 placed upside down relative to the viewing perspective illustrated in FIG. 1A. As best shown by FIG. 1B in conjunction with FIG. 1A the longitudinal length of the resilient tab 106 approximately corresponds to the longitudinal length of the corresponding recess 108. Thus, once in position the resilient tab is locked within the recess and the length of the recess prevents longitudinal movement of the insert 104 within the aperture 103.

As shown, the side walls of the aperture and the terminal wall of the insert 104 defining the viewing window are bevelled, thus enabling the end user to look through the viewing window from a variety of angles.

The device may further include a feature that enables injection of the medicament from the medicament container, such as a needle (not shown) that is positioned at the proximal end of the body 111. Conversely at the distal end 112, there may be located an actuator (not shown), e.g. a button that when depressed activates the injection of the medicament from the medicament container.

Although in the above described exemplary embodiment the insert 104 is fixed within the aperture by use of the resilient tabs 105 & 106 and the corresponding recesses 107 & 108, it will be appreciated that alternate cooperating features may be used. For example, the resilient tabs and corresponding recesses may be located at positions on the insert/side walls of the aperture other than those shown. Alternatively the side walls of the aperture 109 & 110 may comprise one or more resilient tabs which locate in one or more corresponding recesses on the insert 104.

Other cooperating features may be used. For example, the insert may be screwed into position in the aperture, or secured by an expandable rivet. Non-resilient locating tabs on the insert and/or the body may be used which may be rotated to engage with corresponding recesses on the corresponding surfaces of the body or insert. The insert may be a friction fit and/or be glued or heat-welded into position. Other fixing methods will be apparent.

Figure 2A:
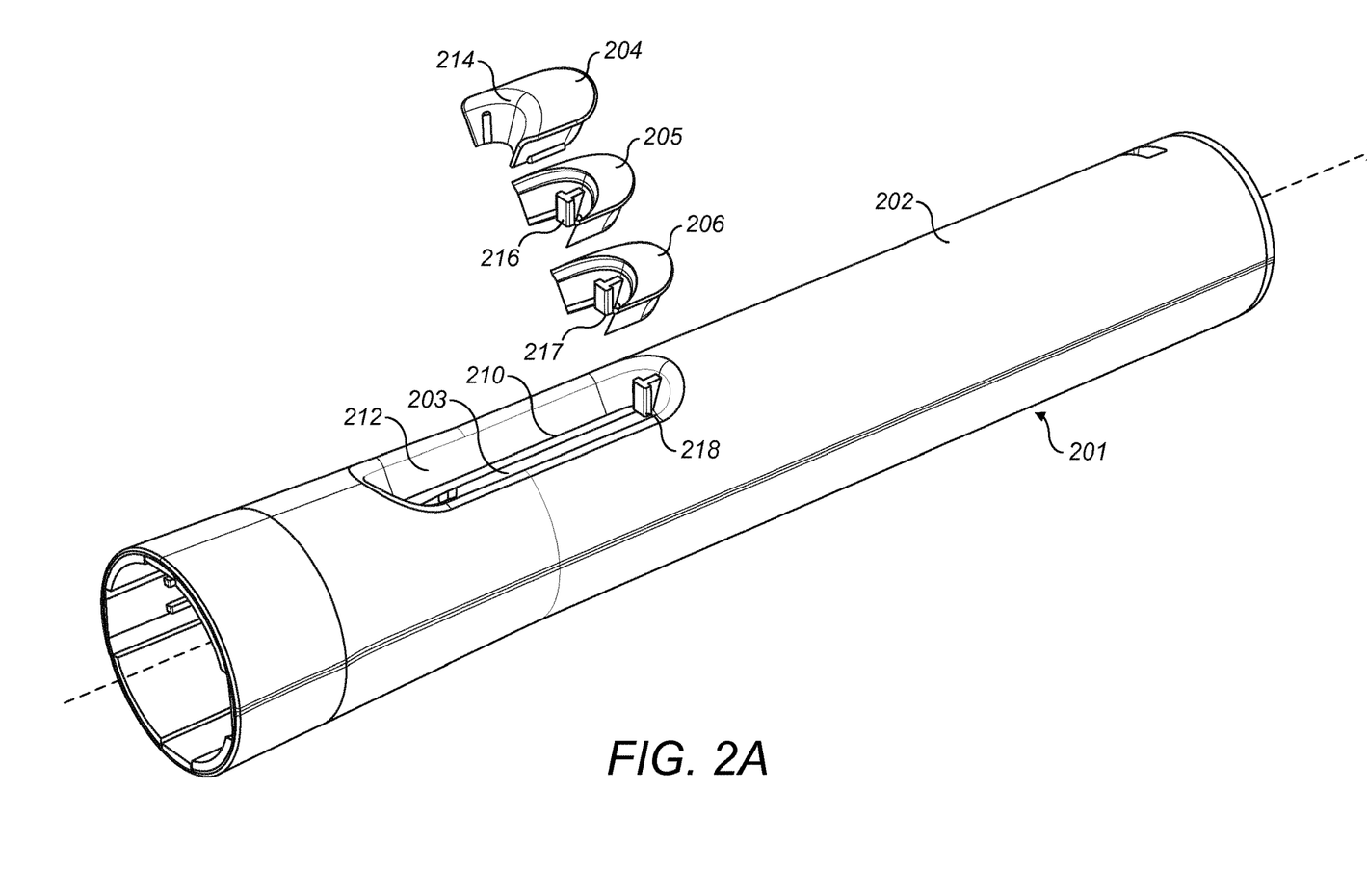
FIG. 2A is a perspective view of a second liquid medicament administration device and corresponding inserts.
Figure 2B:
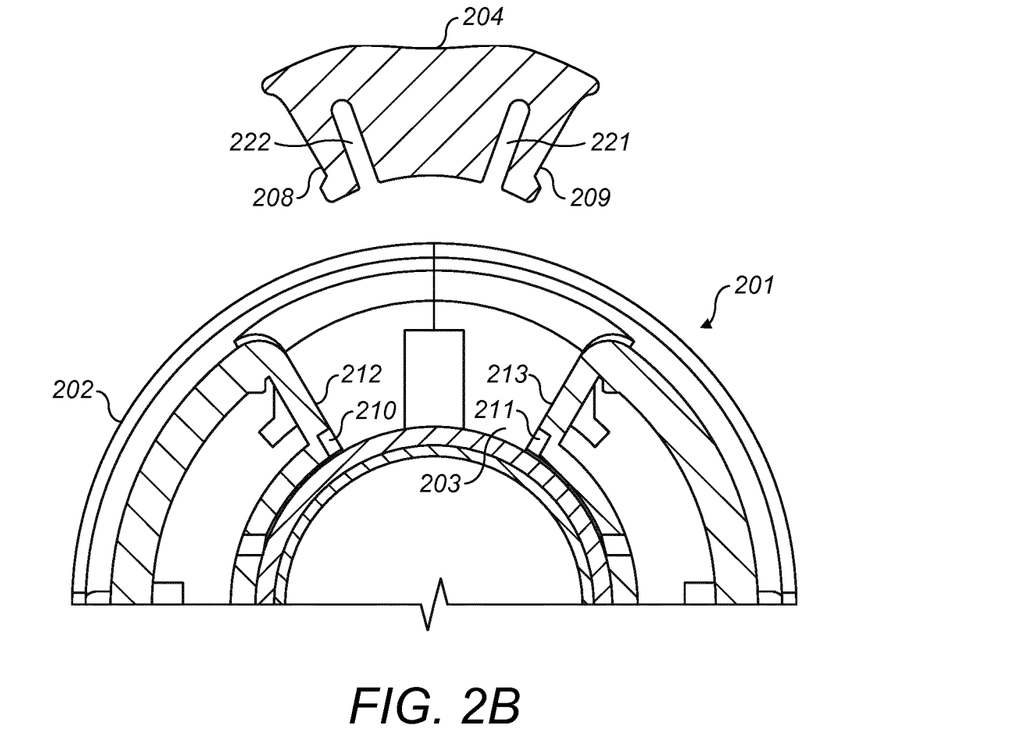
FIG. 2B is a partial cross-sectional view through the second device and an insert at the point of attachment of the insert.
Figure 2C:
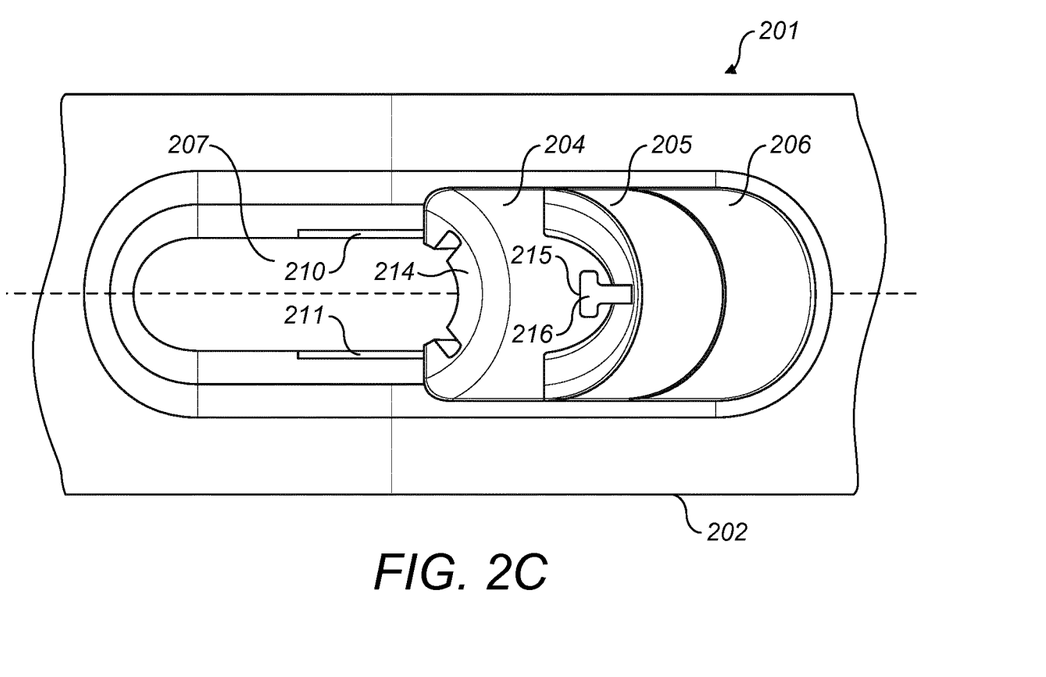
FIG. 2C is a partial top view of the second device with the inserts in position

A second exemplary liquid medicament administration device 201 is shown in FIGS. 2A, 2B & 2C. Again the device comprises a body 202 which forms the outer case of the device. The body further comprises an aperture 203 and the body is configured to contain and support a medicament container (not shown) within the interior of the body 202, in the same manner as discussed in relation to the first exemplary embodiment. The aperture defines a viewing window that enables the medicament container to be viewed when in position. The device further comprises a plurality of inserts 204, 205 & 206 which may be positioned within the aperture so as to reduce the dimensions of the viewing window. The inserts are opaque preventing a view of any empty portion of the medicament container in the unused state.

In order to retain the inserts in the device body, the end insert 204 comprises resilient tabs, e.g. 208 & 209, that engage in corresponding recesses 210 & 211 in the side walls 212 & 213 of the aperture 203. The resilient tabs are thin and rectangular in shape. Relative to the longitudinal axis of the device when the insert 204 is fixed in position, the resilient tabs 208 & 209 have a longitudinal dimension which is greater than their radial dimension which in turn is greater than their tangential dimension. As illustrated in FIG. 2B the resilient tabs 208 & 209 are positioned on the tangential edges of the insert 204 and are attached to the reminder of the insert at a point distal to the longitudinal axis of the device when inserted.

The resilient tabs 208 & 209 comprise protrusions which locate in the corresponding recesses 210 & 211. The protrusions extend outwards tangentially from the resilient tabs, extend along the length of the resilient tabs in a direction approximately parallel to the longitudinal axis of the device X when the insert 204 is in position, and are located at the innermost extremity of the resilient tabs relative to the longitudinal axis of the device X. Again, the resilient tabs are formed from a flexible and resilient material, e.g. plastic, that endows the tabs with their resilient nature.

The insert 204 further comprises cavities 221 & 222 located inboard of the resilient tabs 208 & 209, such that when the insert is pressed into position the resilient tabs may be temporarily deformed inwards into the cavities, before springing outwards into the corresponding recesses 210 & 211, thereby holding the insert in position.

The above-described arrangement of the resilient tabs 208 & 209 and the corresponding recesses 210 & 211 hinders removal of the insert 204 once attached to the body 202. Once in position, there is no access to the resilient tabs 208 & 209 and accordingly the resilient tabs cannot be depressed to facilitate removal. Thus, the insert 204 may only be removed by breakage of the insert 204 and/or the body 202. This discourages interference with the size of the viewing window by the end user or intermediaries.

In this exemplary embodiment, as best shown in FIG. 2c, the recesses 210 & 211 together form a track that extends in a longitudinal direction relative to the longitudinal axis of the device X. Thus the resilient tabs 208 & 209 may locate in the recesses 210 & 211 defining the track at any position along the length of the track. Accordingly, during the manufacturing process the manufacturer has the freedom to select the longitudinal position of the insert 204 within the aperture 203. It will be noted that this first insert 204 has an end face 214, that when in position together with the side walls of the aperture defines the viewing window 207 of restricted size through which the medicament container (not shown) may be observed.

The manufacturer of the device can choose to use a single insert 204 alone, or the single end insert 204 in combination with one or more intermediate inserts, e.g. 205 & 206. In such a manner a wide variation in the size of the viewing window may be achieved depending on the requirements of the medicament container that is to be used. For example, if a large medicament container viewing window is required, the manufacturer may select to use a single insert 204. Conversely, if a smaller medicament container viewing window is desired the manufacturer may select to use a single end insert 204 in combination with a number of intermediate inserts 205 & 206, thus reducing greatly the size of the viewing window 207. The intermediate inserts 205 & 206 and the end insert 204 may be standardised in size. This enables efficiencies to be gained in the manufacture of multiple devices where differing sizes of viewing windows are required. By using the standardised inserts, only one type of intermediate insert 205 or 206, where 205 and 206 are identical, needs to be manufactured, alongside one type of end insert 204. Thus by varying the number of intermediate inserts different sizes of viewing window may be obtained with ease at low cost.

To prevent longitudinal movement of the inserts once inserted, coupling elements and corresponding coupling elements are provided. These are illustrated in FIGS. 2A & 2C. In FIG. 2C, the top cover of the insert 204 is exposed to reveal the coupling element 215 which is a T-shaped recess at the distal end of the insert. Into this recess a corresponding T-shaped connector 216 is fitted. The same T-shaped connectors are provided at the proximal end of each of the intermediate inserts, shown as components 216 & 217 in FIG. 2A, and also at the distal end of the aperture, shown as component 218 in FIG. 2A. Corresponding T-shaped recesses (not shown) are provided in each intermediate insert 205 & 206. As shown, the intermediate inserts 205 & 206 do not engage directly with the recesses 210 & 211 defining the track, but are retained within the aperture by the end insert 204. Alternatively however the intermediate inserts 205 & 206 may also comprise resilient tabs which are able to engage with the track provided by the two recesses 210 & 211. As will be appreciated, the combination of the T-shaped connectors and the track with the corresponding resilient tabs means that the inserts and the intermediate inserts can be pushed into position from a direction approximately orthogonal to the longitudinal axis of the device X. Once in position, the T-shaped connectors prevent movement of the inserts in a longitudinal direction.

Although in the above described exemplary embodiment a T-shaped connector and a corresponding T-shaped recess is used, it will be appreciated that other types of connectors may be used to prevent movement of the inserts in a longitudinal direction. For example, L-shaped connectors and corresponding L-shaped recesses could be used. Alternatively hooks may be provided at the distal end of the aperture and the proximal ends of the intermediate inserts, and corresponding holes or loops for receiving the hooks at the distal end of the inserts.

In another alternative, the coupling elements and corresponding coupling elements may be configured such that the inserts may be attached to the track, then slid in a longitudinal direction so as to effect the coupling. For example, a barbed element may be provided at the distal end of the aperture onto which an insert having a corresponding receiving cavity may be slid. Once inside the cavity, the barb locates on an opposing face, preventing withdrawal. Alternatively the barbed element may be attached to the insert and the corresponding receiving cavity located at the distal end of the aperture.

Figure 3:
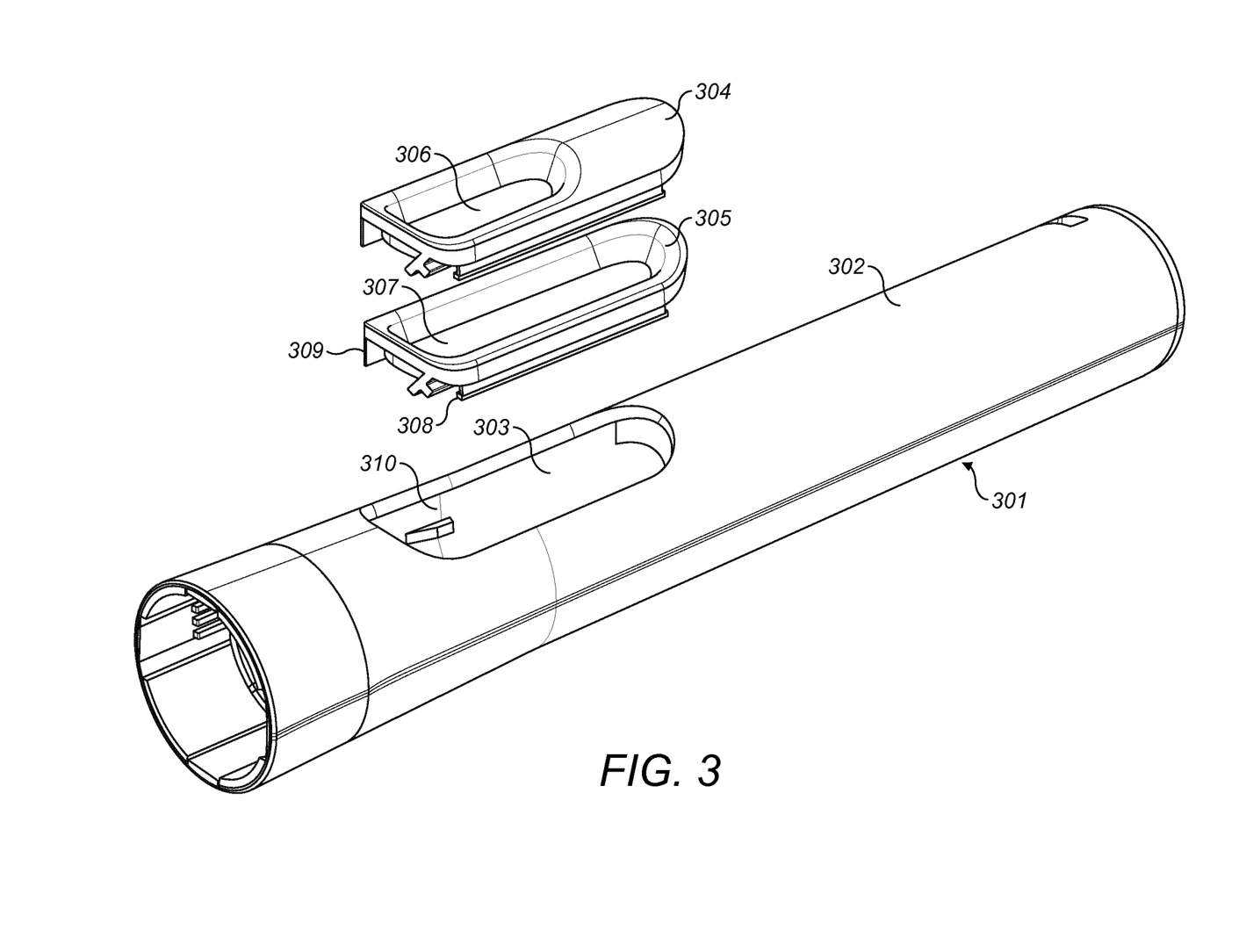
FIG. 3 is a perspective view of a third liquid medicament administration device and corresponding inserts.

A third exemplary embodiment is shown in FIG. 3. In this instance a device 301 is provided comprising a body 302 which also forms the outer case of the device. The body comprises an aperture 303 which defines a viewing window enabling a medicament container (not shown) to be viewed when in position in the body of the device. The medicament container may be located within the body 302 in the same manner as discussed in relation to the first exemplary embodiment.

Alternate inserts 304 & 305 are provided which fit in the aperture 303. The inserts comprise apertures 306 & 307 of differing dimensions. Once in position the inserts reduce the size of the viewing window 303 to a greater or lesser extent depending on the dimensions of the apertures 306 & 307. Once inserted the dimensions of the viewing window are defined entirely by the dimensions of the apertures 306 & 307. The outer dimensions of the inserts 304 & 305 are identical thus enabling different inserts to be selected for use with the same outer casing 302. Again, the inserts comprise resilient tabs 308 & 309 which engage with corresponding recesses, e.g. 310, in the body of the device thus securing the inserts in position. The inserts and corresponding recesses may be as described in relation to either of the two preceding exemplary embodiments.

Figure 4A:
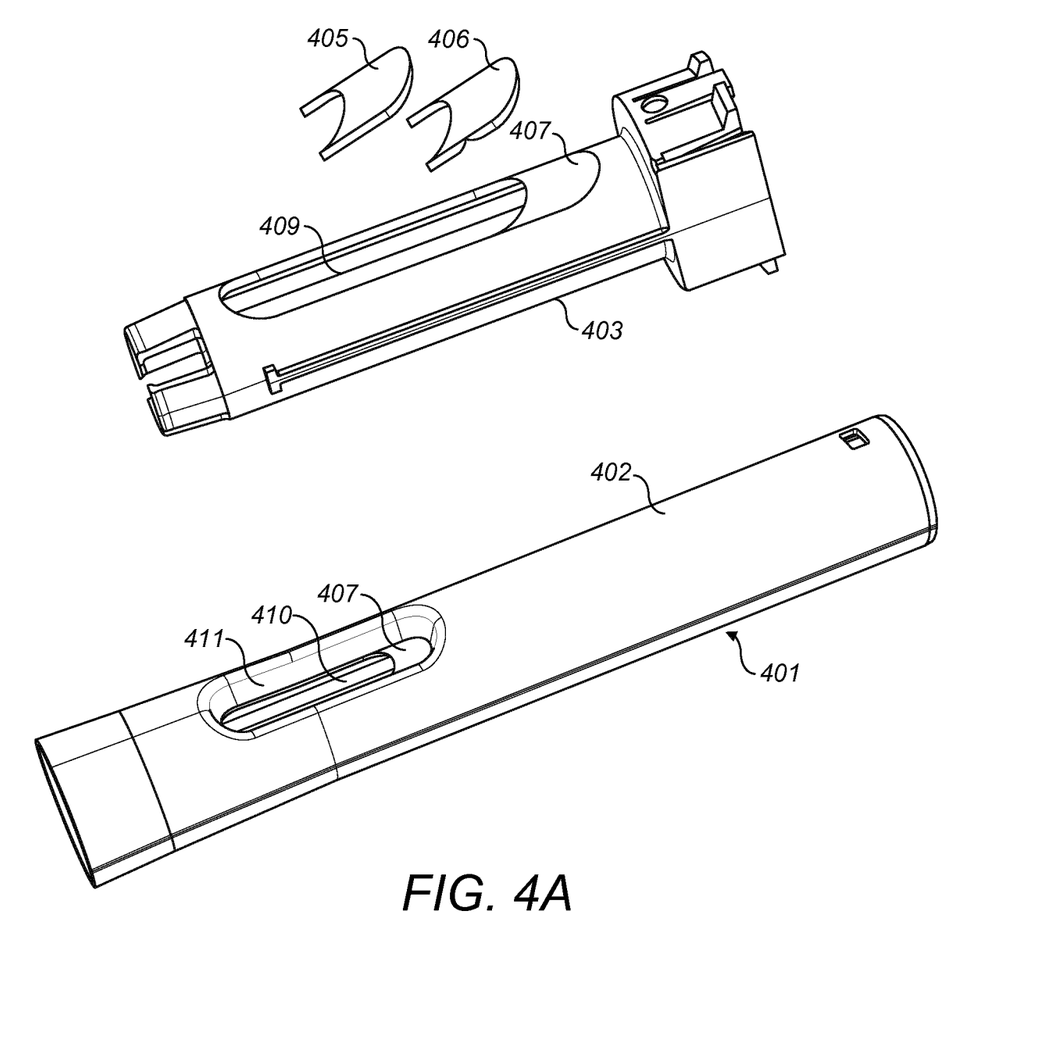
FIG. 4A is perspective view of a fourth liquid medicament administration device and a corresponding inner carrier with breakable segments removed.
Figure 4B:
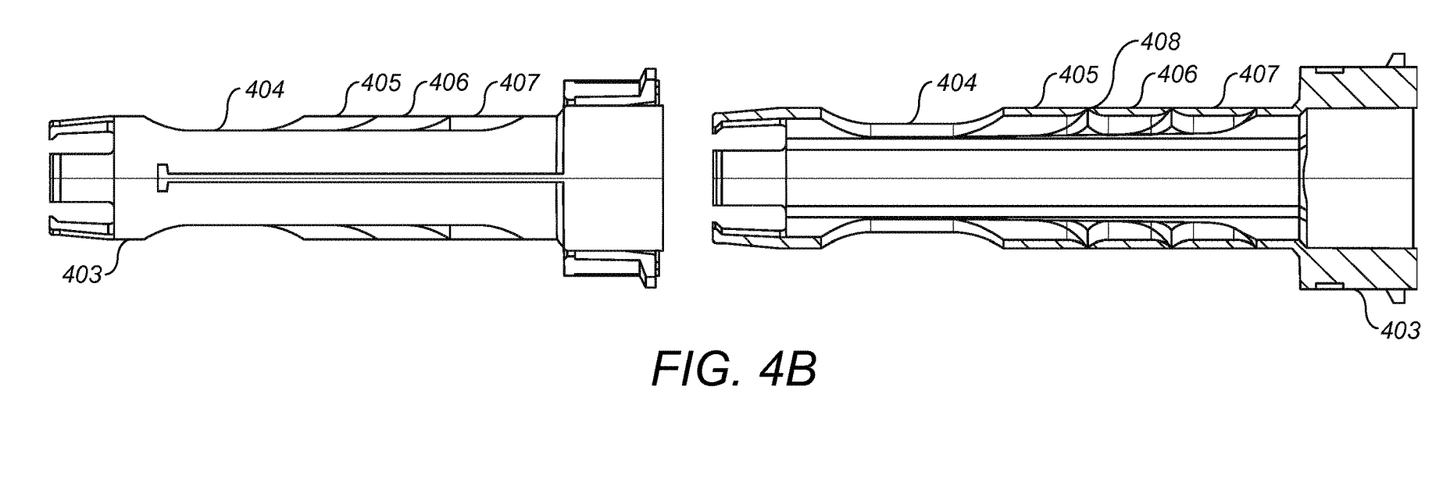
FIG. 4B includes a side and a side cross-sectional view of the internal carrier of FIG. 4A with the breakable segments attached.

A fourth exemplary embodiment is illustrated in FIGS. 4A & 4B. In this embodiment, the device comprises an outer case 402 and a body 403 forming an inner carrier. The inner carrier is locatable within the outer case. The inner carrier comprises an aperture 404. The inner carrier is configured to contain and support a medicament container such as a syringe therein, such that the medicament container may be viewed through a viewing window defined by the aperture 404. Where the medicament container is a syringe, typically the portion of the syringe cylinder proximal to the exit port may be viewed through the viewing window.

The inner carrier further comprises a number of removable segments 405, 406 & 407, which may be removed so as to extend the dimensions of the aperture. In FIG. 4B, the removable segments are shown in place on the carrier, while two segments 405 & 406 are removed in FIG. 4A. The segments are connected to each other and to the remainder of the carrier by breakable elements such as thin walled plastic 408. Thus the manufacturer of the device may simply break off the required number of removable segments to extend the aperture 404 to the desired length. This results in an extended aperture 409.

Other breakable elements may be used. For example, breakable plastic strands connecting the removable segments to the inner carrier may be employed. Alternatively the removable segments may be attached to the inner carrier using glue of sufficiently low tack that the bond may be broken without damage to the inner carrier.

It is also envisaged that non-breakable elements may be used to secure the removable segments to the inner carrier. For example, the removable segments may be secured by releasable fasteners, or may be secured via locating pegs engaging in corresponding holes or cavities in the removable segments.

After the removal of the required number of segments, the inner carrier 403 is placed within the outer case 402. As can be seen, the outer case 402 comprises a second aperture defined by side walls 411. The apertures of the inner carrier and the outer carrier coincide, such that a viewing window 410 is defined through which the quantity of the medicament in the medicament container when present may be viewed. As illustrated in the lower diagram in FIG. 4A, the terminal removable segment 407 has been left in position, thus when the inner carrier is inserted the dimensions of the viewing window 410 are defined partially by the side walls 411 of the second aperture in the outer case and partially by the dimensions of the extended inner aperture 409 of the inner carrier.

The second aperture in the outer case 402 is elongate and the tangential width of this second aperture is less than the tangential width of the removable segments, such that the removal of any remaining removable segments of the inner carrier is prevented once the inner carrier has been inserted. This prevents interference with the size of the viewing window by the end user.

As disclosed in the relation to any of the above described embodiments, the body, one or more inserts, one or more removable segments, inner carrier and/or outer case are typically formed from plastic, e.g. by moulding.

The medicament container, as used in relation to any embodiment described herein, may be a sealed cartridge, such as a glass vial sealed by a film, configured such that the seal is broken on actuation of the device. Alternatively, the medicament container may be a syringe, where the medicament is stored in a hollow cylinder, typically formed of glass or transparent plastic. The medicament is sealed from the environment by a piston moveable within the cylinder. The piston is connected to a piston rod for operating the piston. The syringe further comprises an exit port in fluid communication with the inside of the cylinder, located distal to the piston. Typically the exit port is sealed, e.g. by a film, until use. The exit port seal may be broken on actuation of the device. Alternatively a needle may be fluidly connected to the exit port and the needle capped until use in order to maintain the medicament under sterile conditions.

Typically, a tubular delivery component such as a needle or a cannula is provided to deliver the liquid medicament from the medicament container to the patient. In the above-described embodiments, the tubular delivery component is attachable at the proximal end of the device. The tubular delivery device may be configured to pierce a seal of the medicament container on activation or attachment. For example, the tubular delivery device may comprise a double-ended needle. One end of the double ended needle may be used to pierce the skin of the patient and the other the seal of the medicament container.

The liquid medicament administration device, as described herein, is typically a liquid medicament injection device. Typically, the device is configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.1 ml to about 2 ml, more typically from about 0.5 ml to about 1 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The medicament administration devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle sleeve in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Where a device of the present disclosure includes an energy source and/or an activation component, typically such energy sources and/or activation components are located within or at the distal end of the device.

Typically, the medicament is a liquid medicament. Alternatively the medicament may be a reconstitutable medicament suitable for forming a liquid medicament. The liquid medicament may be a solution or a suspension formulation. Typically the liquid medicament is suitable for injection.

The terms "drug" or "medicament" which are used interchangeably herein, mean a pharmaceutical formulation that includes at least one pharmaceutically active compound.

The term "drug delivery device" shall be understood to encompass any type of device, system or apparatus designed to immediately dispense a drug to a human or non-human body (veterinary applications are clearly contemplated by the present disclosure). By "immediately dispense" is meant an absence of any necessary intermediate manipulation of the drug by a user between discharge of the drug from the drug delivery device and administration to the human or non-human body. Without limitation, typical examples of drug delivery devices may be found in injection devices, inhalers, and stomach tube feeding systems. Again without limitation, exemplary injection devices may include, e.g., syringes, autoinjectors, injection pen devices and spinal injection systems.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine. Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na$^+$, or K$^+$, or Ca$^{2+}$, or an ammonium ion N$^+$(R$^1$)(R$^2$)(R$^3$)(R$^4$), wherein R$^1$ to R$^4$ independently of each other mean: hydrogen, an optionally substituted $C_1$-$C_6$-alkyl group, an optionally substituted $C_2$-$C_6$-alkenyl group, an optionally substituted $C_6$-$C_{10}$-aryl group, or an optionally substituted $C_6$-$C_{10}$-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof

The invention claimed is:

1. A system comprising:
   a liquid administration device; and
   one or more inserts;
   wherein the liquid administration device comprises a body configured to contain and support a medicament container;
   wherein the body comprises a wall;
   wherein the liquid administration device comprises a proximal end and a distal end, with a longitudinal axis extending from the proximal end to the distal end;
   wherein the medicament container comprises an initial quantity of a medicament;
   wherein the wall of the body comprises a viewing window in the form of an aperture;
   wherein the aperture has a longitudinal dimension parallel to the longitudinal axis of the device;
   wherein, when the medicament container is contained and supported by the body, the viewing window is coincident with the medicament container such that the medicament is visible through the viewing window; and
   wherein the aperture is configured to receive the one or more inserts, wherein the one or more inserts, when received by the aperture, reduce the longitudinal dimension of the aperture so as to partially obscure the aperture and hence reduce the size of the viewing window prior to the medicament being dispensed from the medicament container.

2. The system of claim 1, wherein the one or more inserts comprise one or more resilient tabs that engage in one or more corresponding recesses in one or more side walls defining the aperture.

3. The system of claim 1, wherein the aperture is elongate and comprises a first side wall and a second side wall, wherein each of the first and second side walls extends in an approximately parallel direction relative to the longitudinal axis of the liquid administration device, wherein the first side wall comprises a first recess for engaging a first resilient tab and the second side wall comprises a second recess for engaging a second resilient tab, and wherein the one or more inserts comprise a first insert comprising both the first and the second resilient tabs.

4. The system of claim 3, wherein a longitudinal length of at least one of the first or second recesses substantially corresponds to a length of the corresponding first or second resilient tab that engages with the recess, such that the first insert attached to the corresponding first or second resilient tab is prevented from moving in a longitudinal direction.

5. The system of claim 3, wherein the first and the second recesses together form a track extending in an approximately longitudinal direction relative to the longitudinal axis of the liquid administration device, wherein the first and second resilient tabs of the first insert are able to engage with the track at any position along its length, and wherein the first insert further comprises a coupling element adapted to engage with a corresponding coupling element at a terminal end of the aperture to prevent movement of the first insert in a longitudinal direction.

6. The system of claim 5, wherein the coupling element is adapted to engage with the corresponding coupling element at the terminal end of the aperture via one or more intermediate inserts to prevent movement of the first insert in the longitudinal direction.

7. The system of claim 5, wherein the aperture is configured to receive one or more intermediate inserts, wherein each intermediate insert comprises:
   a coupling element that is substantially identical to the coupling element of the first insert; and
   a corresponding coupling element that is substantially identical to the corresponding coupling element at the terminal end of the aperture.

8. The system of claim 1, wherein one of the one or more inserts comprises an aperture which exclusively defines the dimensions of the size-adjusted viewing window.

9. The system of claim 1, wherein the body forms an outer case of the liquid administration device.

10. The system of claim 1, wherein the liquid administration device is configured such that an end-size of the viewing window is predetermined in relation to the initial quantity of the medicament in the medicament container.

11. The system of claim 1, wherein the liquid administration device is configured such that the size of the viewing window is adjustable from a first size in which a plunger rod or a stopper of the medicament container is viewable through the viewing window to a second size in which the plunger rod or the stopper is obscured from being viewed through the viewing window.

12. The system of claim 1, wherein the liquid administration device is configured such that the size of the viewing window is fixed while the medicament is dispensed from the medicament container.

13. The system of claim 12, wherein the liquid administration device is configured such that the medicament container is visible through the majority of the viewing window for the entire duration of the medicament dispensing procedure.

14. The system of claim 1, wherein the aperture has received the one or more inserts.

15. A liquid medicament administration device comprising:
   a body configured to contain and support a medicament container;
   wherein the medicament container comprises an initial quantity of a medicament;
   wherein the body comprises a wall;
   wherein the liquid medicament administration device comprises a proximal end and a distal end, with a longitudinal axis extending from the proximal end to the distal end;
   wherein the wall of the body comprises a viewing window in the form of an aperture;

wherein the aperture has a longitudinal dimension parallel to the longitudinal axis of the liquid medicament administration device;

wherein, when the medicament container is contained and supported by the body, the viewing window is coincident with the medicament container such that the medicament is visible through the viewing window;

wherein the wall of the body comprises one or more removable segments adjacent to the aperture and at least partially defining the longitudinal dimension of the aperture, the one or more removable segments being configured to extend the longitudinal dimension of the aperture upon removal to increase a size of the viewing window prior to the medicament being dispensed from the medicament container.

16. The device of claim 15, wherein each of the one or more removable segments are attached to the wall of the body via one or more breakable elements.

17. The device of claim 15, wherein the body forms an inner carrier within an outer case, wherein the outer case comprises a second aperture, and wherein both the aperture of the body and the second aperture of the outer case comprise the viewing window.

18. The device of claim 1, wherein the liquid medicament administration device comprises the medicament container, the medicament container containing the medicament.

19. The device of claim 1, wherein the medicament container is a syringe.

20. The liquid medicament administration device of claim 15, wherein the liquid medicament administration device is configured such that the size of the viewing window is fixed while the medicament is dispensed from the medicament container.

21. The system of claim 20, wherein the liquid medicament administration device is configured such that the medicament container is visible through the majority of the viewing window for the entire duration of the medicament dispending procedure.

22. A method of manufacturing a liquid medicament administration device, the method comprising:

providing a liquid medicament administration device comprising a body configured to contain and support a medicament container, wherein the body comprises a wall, wherein the liquid medicament administration device comprises a proximal end and a distal end, with a longitudinal axis extending from the proximal end to the distal end, wherein the medicament container comprises an initial quantity of a medicament, wherein the wall of the body comprises a viewing window in the form of an aperture, wherein the aperture has a longitudinal dimension parallel to the longitudinal axis of the liquid medicament administration device, wherein when the medicament container is contained and supported by the body, the viewing window is coincident with the medicament container such that the medicament is visible through the viewing window when the medicament container is contained and supported by the body; and adjusting a size of the viewing window prior to the medicament being dispensed from the medicament container in relation to the initial quantity of the medicament in the medicament container, said adjustment comprising either:
(i) receiving, by the aperture, one or more inserts to reduce the longitudinal dimension of the aperture so as to partially obscure the aperture and hence reduce the size of the viewing window; or
(ii) removing one or more removable segments from the wall of the body, the one or more removeable elements being adjacent to the aperture and at least partially defining the longitudinal dimension of the aperture, wherein said removal increases the longitudinal dimension of the aperture and hence increases the size of the viewing window.

23. The method of claim 22, wherein adjusting the size of the viewing window comprises receiving, by the aperture, one or more inserts to reduce the longitudinal dimension of the aperture so as to partially obscure the aperture and hence reduce the size of the viewing window.

24. The method of claim 23, wherein:
the aperture is elongate and comprises:
a first side wall comprising a first recess; and
a second side wall comprising a second recess, wherein each of the first and second side walls extend in an approximately parallel direction relative to the longitudinal axis of the liquid medicament administration device;
the one or more inserts comprise a first insert comprising a first resilient tab and a second resilient tab; and
receiving the one or more inserts comprises:
engaging, by the first recess of the first side wall, the first resilient tab of the first insert; and
engaging, by the second recess of the second side wall, the second resilient tab of the first insert.

25. The method of claim 24, wherein the first and the second recesses together form a track extending in an approximately longitudinal direction relative to the longitudinal axis of the liquid medicament administration device, wherein the first and second resilient tabs of the first insert are able to engage with the track at any position along its length, wherein the first insert further comprises a coupling element, and wherein the method further comprises engaging the coupling element with a corresponding coupling element at a terminal end of the aperture to prevent movement of the first insert in a longitudinal direction.

26. The method of claim 22, wherein adjusting the size of the viewing window comprises the step of removing the one or more removable segments from the wall of the body, the one or more removeable elements being adjacent to the aperture and at least partially defining the longitudinal dimension of aperture, wherein said removal increases the longitudinal dimension of the aperture and hence increases the size of the viewing window.

* * * * *